United States Patent
Sharifi et al.

(10) Patent No.: US 10,912,906 B2
(45) Date of Patent: Feb. 9, 2021

(54) MECHANICAL VENTILATION WITH AUTOMATIC CONTROL OF PATIENT'S WORK OF BREATHING USING CLASSICAL FEEDBACK CONTROL

(71) Applicant: KONINKLIJKE PHILIPS N.V., Eindhoven (NL)

(72) Inventors: Mahmoudreza Sharifi, Croton-On-Hudson, NY (US); Nicolas Wadih Chbat, White Plains, NY (US)

(73) Assignee: Koninklijke Philips N.V., Eindhoven (NL)

( * ) Notice: Subject to any disclaimer, the term of this patent is extended or adjusted under 35 U.S.C. 154(b) by 260 days.

(21) Appl. No.: 15/767,734

(22) PCT Filed: Oct. 11, 2016

(86) PCT No.: PCT/EP2016/074342
§ 371 (c)(1),
(2) Date: Apr. 12, 2018

(87) PCT Pub. No.: WO2017/064061
PCT Pub. Date: Apr. 20, 2017

(65) Prior Publication Data
US 2018/0289911 A1 Oct. 11, 2018

Related U.S. Application Data

(60) Provisional application No. 62/240,147, filed on Oct. 12, 2015.

(51) Int. Cl.
*A61M 16/00* (2006.01)
*G16H 40/63* (2018.01)
(Continued)

(52) U.S. Cl.
CPC .......... *A61M 16/026* (2017.08); *A61B 5/085* (2013.01); *A61B 5/087* (2013.01); *A61B 5/4836* (2013.01);
(Continued)

(58) Field of Classification Search
CPC ............ A61M 16/026; A61M 16/0051; G16H 20/40; G16H 40/63; A61B 5/085;
(Continued)

(56) References Cited

U.S. PATENT DOCUMENTS 5,303,698 A 4/1994 Tobia et al.
6,390,091 B1 5/2002 Banner et al.
(Continued)

FOREIGN PATENT DOCUMENTS

WO 0220076 A2 3/2002
WO 2009115949 A1 9/2009
(Continued)

*Primary Examiner* — Kendra D Carter
*Assistant Examiner* — Jonathan S Paciorek
(74) *Attorney, Agent, or Firm* — Daniel H. Brean

(57) ABSTRACT

A mechanical ventilator (10) provides pressure support ventilation (PSV) to a patient (12). A power of breathing (PoB) or work of breathing (WoB) estimator (30) generates a PoB or WoB signal (34) for the patient. An error calculator (36) computes an error signal as a difference between the PoB or WoB signal and a set point PoB or WoB value (22). A controller (20) inputs a PSV control signal (24) equal to the product of the controller transfer function and the error signal to the mechanical ventilator. A patient adaptation component (52, 54, 56, 60) fits parameters of a model of a controlled mechanical ventilation system comprising the mechanical ventilator and the patient to data comprising the PoB or WoB signal and the PSV control signal generated by the operating closed loop controller, and adjusts parameters
(Continued)

of the controller transfer function to maintain stability of the operating closed loop controller.

12 Claims, 11 Drawing Sheets

(51) Int. Cl.
| | | |
|---|---|---|
| *A61B 5/085* | (2006.01) | |
| *A61B 5/087* | (2006.01) | |
| *A61B 5/00* | (2006.01) | |
| *G16H 20/40* | (2018.01) | |
| *A61B 5/08* | (2006.01) | |

(52) U.S. Cl.
CPC ........ *A61M 16/0051* (2013.01); *G16H 20/40* (2018.01); *G16H 40/63* (2018.01); *A61B 5/0816* (2013.01); *A61B 5/725* (2013.01); *A61M 2016/003* (2013.01); *A61M 2016/0015* (2013.01); *A61M 2016/0027* (2013.01); *A61M 2205/3331* (2013.01); *A61M 2205/50* (2013.01); *A61M 2205/52* (2013.01); *A61M 2230/06* (2013.01); *A61M 2230/40* (2013.01); *A61M 2230/42* (2013.01); *A61M 2230/432* (2013.01); *A61M 2230/46* (2013.01)

(58) Field of Classification Search
CPC ..... A61B 5/087; A61B 5/4836; A61B 5/0816; A61B 5/725
See application file for complete search history.

(56) References Cited

U.S. PATENT DOCUMENTS

| | | | |
|---|---|---|---|
| 2007/0151563 A1 | 7/2007 | Ozaki et al. | |
| 2013/0263855 A1* | 10/2013 | Tivig | ............... A61B 5/746 128/204.23 |
| 2013/0276787 A1 | 10/2013 | Martin et al. | |
| 2014/0276173 A1 | 9/2014 | Banner et al. | |
| 2015/0059754 A1* | 3/2015 | Chbat | ............... A61B 5/087 128/204.23 |
| 2015/0090264 A1 | 4/2015 | Dong | |
| 2015/0157816 A1 | 6/2015 | Freeman et al. | |

FOREIGN PATENT DOCUMENTS

| | | | | |
|---|---|---|---|---|
| WO | 2012156885 A1 | 11/2012 | | |
| WO | 2013067580 A1 | 5/2013 | | |
| WO | WO-2013144925 A1 * | 10/2013 | ............ | A61B 5/087 |
| WO | 2014207623 A2 | 12/2014 | | |
| WO | 2016166709 A1 | 10/2016 | | |

\* cited by examiner

MECHANICAL VENTILATION WITH AUTOMATIC CONTROL OF PATIENT'S WORK OF BREATHING USING CLASSICAL FEEDBACK CONTROL

CROSS-REFERENCE TO PRIOR APPLICATIONS

This application is the U.S. National Phase application under 35 U.S.C. § 371 of International Application No. PCT/EP2016/074342, filed on Oct. 11, 2016, which claims the benefit of U.S. Provisional Patent Application No. 62/240,147, filed on Oct. 12, 2015, applications are hereby incorporated by reference herein.

FIELD

The following relates generally to the mechanical ventilation arts, respiratory health arts, and related arts.

BACKGROUND

Mechanical ventilators are life-saving machines that help patients with impaired respiratory drive, or lack of respiratory drive, on a temporary or long term basis. In both cases, the level of respiratory support strongly impacts patient outcome. It is estimated that about 1-in-5 patients who receive mechanical ventilation develop some form of ventilator-related lung injury attributable to the ventilator providing too much support. Another problem with the providing too much ventilator support is that the patient may become overly dependent on the ventilator machine, which can lead to more difficult wean-off from the ventilator and longer recovery time for the patient. On the other hand, if the ventilator provides too little support, then the patient over-exerts to breathe producing detrimental patient stress. Too little ventilation support can also lead to insufficient respiration and potential adverse conditions such as hypoxia.

In the case of a patient who is unable to spontaneously breath, a ventilation mode such as continuous mandatory ventilation (CMV) is typically employed. In CMV, the ventilator initiates mandatory breaths at a programmed respiration rate, and each mandatory breath is driven to a pre-set inflation volume by action of the mechanical ventilator. This ensures adequate ventilation, but it is difficult to later wean the patient off the ventilator as CMV does not support any spontaneous respiration effort by the patient.

In the case of a patient who is spontaneously breathing, the goal of mechanical ventilation is to support the spontaneous respiration without providing too much support. Mechanical ventilation using pressure support, i.e. Pressure Support Ventilation (PSV), is a common operating mode for supporting spontaneous breathing. In PSV, the ventilator controller detects the onset of spontaneous inspiration as a decrease in airway pressure or an abrupt increase in air flow. The ventilator then applies pressure at a PSV pressure setting to support the patient's spontaneous inhalation effort. In PSV, the patient controls respiration rate and inflation volume, with the mechanical ventilator being limited to providing pressure support at the PSV pressure setting to assist the spontaneous breaths. PSV is thus well-suited to providing ventilator assistance for a spontaneously breathing patient.

When PSV is used alone, the patient initiates all breaths. This is beneficial to encourage the patient's respiratory effort, but PSV cannot provide effective ventilation if the patient fails to spontaneously initiate breaths at a sufficient rate. To provide a safety net, PSV may be combined with an intermittent mandatory ventilation (IMV) mode that triggers ventilator-driven (i.e. mandatory) breaths if the spontaneous breaths alone are determined by the ventilator to provide insufficient ventilation for the patient.

Typical ventilator settings of a ventilator operating in a PSV or PSV/IMV mode include the PSV pressure setting, one or more trigger parameters (specifying how the ventilator detects spontaneous breaths), one or more mandatory breath cycling parameters (controlling timing of IMV-initiated mandatory breaths), and fraction of inspired oxygen ($FiO_2$, for oxygenated patients). These ventilator settings are prescribed by the physician. During mechanical ventilation, airway pressure and flow, fraction or percent of respired carbon dioxide ($CO_2$, via capnography, e.g. end-tidal $CO_2$ or $etCO_2$), heart rate, respiratory rate, peripheral capillary oxygen saturation ($SpO_2$), and/or so forth are monitored. During physician visits to the patient's hospital room (usually occurring one or more times per day), the prescribed ventilator settings may be adjusted based on the patient's current condition as indicated by the various physiological measurements.

However, the patient's condition may change significantly between successive physician visits. This can lead to the patient being mechanically ventilated under significantly non-optimal ventilator settings until the next physician visit. Ventilation using non-optimal ventilator settings, in turn, enhances the likelihood of ventilator-related lung injury.

Chbat et al., U.S. Pub. No. 2015/0059754 published Mar. 5, 2015 discloses an improvement in which the patient's Power of Breathing (PoB) is estimated in real-time and, if different from a physician-prescribed PoB, one or more ventilator setting adjustments are made (optionally automatically) based on the identified PoB difference. The ventilator setting adjustments may include, for example, changing settings such as tidal volume, respiratory rate, pressure readings, airflow, or so forth, and/or may also include changes to an operating mode of the ventilator. The approach of Chbat et al. is generally applicable to ventilator modes including but not limited to: volume controlled continuous mandatory ventilation, volume controlled intermittent mandatory ventilation, pressure controlled continuous mandatory ventilation, pressure controlled intermittent mandatory ventilation, continuous spontaneous ventilation, high frequency ventilation systems, or so forth.

The following discloses a new and improved systems and methods that address the above referenced issues, and others.

SUMMARY

Notwithstanding the foregoing, there remains a need in the art to provide improved automated ventilator control for spontaneously breathing patients, which can rapidly adapt to changes in the patient's physiological condition, is readily implemented, and is easily comprehended by the physician and nursing staff.

In one disclosed aspect, a respiratory therapy device comprises: a mechanical ventilator configured to provide mechanical ventilation to a patient in a pressure support ventilation (PSV) or pressure support ventilation/intermittent mandatory ventilation (PSV/IMV) mode in accordance with a PSV pressure setting; a power of breathing (PoB) or work of breathing (WoB) estimator configured to generate a PoB or WoB signal for the patient; an error calculator configured to compute an error signal E(s) as a difference between the PoB or WoB signal and a set point PoB or WoB value; and a controller having a controller transfer function C(s) and configured to input the PSV pressure setting equal to C(s)E(s) to the mechanical ventilator. By way of illustration, the mechanical ventilator, the PoB or WoB estimator, the error calculator, and the controller may be operatively interconnected to form a single-input, single-output (SISO) closed loop feedback control system in which the mechanical ventilator and a connected patient and the PoB or WoB estimator define the controlled system whose single input is the PSV pressure setting and whose single controlled output is the PoB or WoB signal. The respiratory therapy device may further include a patient adaptation component comprising an electronic device programmed to fit parameters of a model of the controlled system transfer function to PoB or WoB signal and PSV pressure setting data generated by the operating SISO closed loop feedback control system and to adjust parameters of the controller transfer function C(s) to maintain stability of the closed loop transfer function of the SISO closed loop feedback control system.

In another disclosed aspect, a single input, single output (SISO) closed loop controller is disclosed for controlling a mechanical ventilator configured to provide mechanical ventilation to a patient in a PSV or PSV/IMV mode in accordance with a PSV pressure setting. The closed-loop controller comprises: a PoB or WoB estimator configured to generate a signal representing PoB or WoB of the patient; an error calculator configured to compute an error signal E(s) as a difference between the signal representing PoB or WoB of the patient and a set point value; and a controller having a controller transfer function C(s) and configured to generate the PSV pressure setting as the product C(s)E(s). In some embodiments the SISO closed loop controller further comprises a patient adaptation component comprising an electronic device programmed to fit parameters of a model of the controlled system transfer function $$G(s) = \frac{PoB(s)}{PSV(s)}$$

of a ventilator providing ventilation to a patient under control of the SISO closed-loop controller to PoB(s) and PSV(s) data generated by the operating SISO closed loop controller and to adjust parameters of the controller transfer function C(s) to maintain stability of the closed loop transfer function $$\frac{C(s)G(s)}{1 + C(s)G(s)}.$$

In another disclosed aspect, a closed loop controller is disclosed for controlling a mechanical ventilator configured to provide mechanical ventilation to a spontaneously breathing patient. The closed-loop controller comprises: a PoB or WoB estimator configured to generate a PoB or WoB signal for the patient; an error calculator configured to compute an error signal E(s) as a difference between the PoB or WoB signal and a set point PoB or WoB value; a controller having a controller transfer function C(s) and configured to input a pressure support ventilation (PSV) control signal equal to the product C(s)E(s) to the mechanical ventilator to control the mechanical ventilation provided to the spontaneously breathing patient; and a patient adaptation component comprising an electronic device programmed to fit parameters of a model of a controlled mechanical ventilation system comprising a ventilator and a spontaneously breathing patient ventilated by the mechanical ventilator under control of the closed loop controller to data comprising the PoB or WoB signal and the PSV control signal generated by the operating closed loop controller and to adjust parameters of the controller transfer function C(s) to maintain stability of the operating closed loop controller.

In another disclosed aspect, a closed loop control method is disclosed for controlling mechanical ventilation provided by a mechanical ventilator to a spontaneously breathing patient. The closed-loop control method comprises: measuring a PoB or WoB signal for the patient being provided mechanical ventilation; computing an error signal as a difference between the measured PoB or WoB signal and a set point PoB or WoB value; and setting pressure support of the mechanical ventilation to a control signal computed as a product of a controller transfer function and the error signal.

One advantage resides in providing improved automated ventilator control for mechanically ventilated spontaneously breathing patients.

Another advantage resides in providing such automated ventilator control with physician-prescribed constraints having physiological bases.

Another advantage resides in providing such automated ventilator control that is adaptive to changing patient condition.

Another advantage resides in providing such automated ventilator control that is robust against noise and system disturbances.

Another advantage resides in providing such automated ventilator control with zero steady state error.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
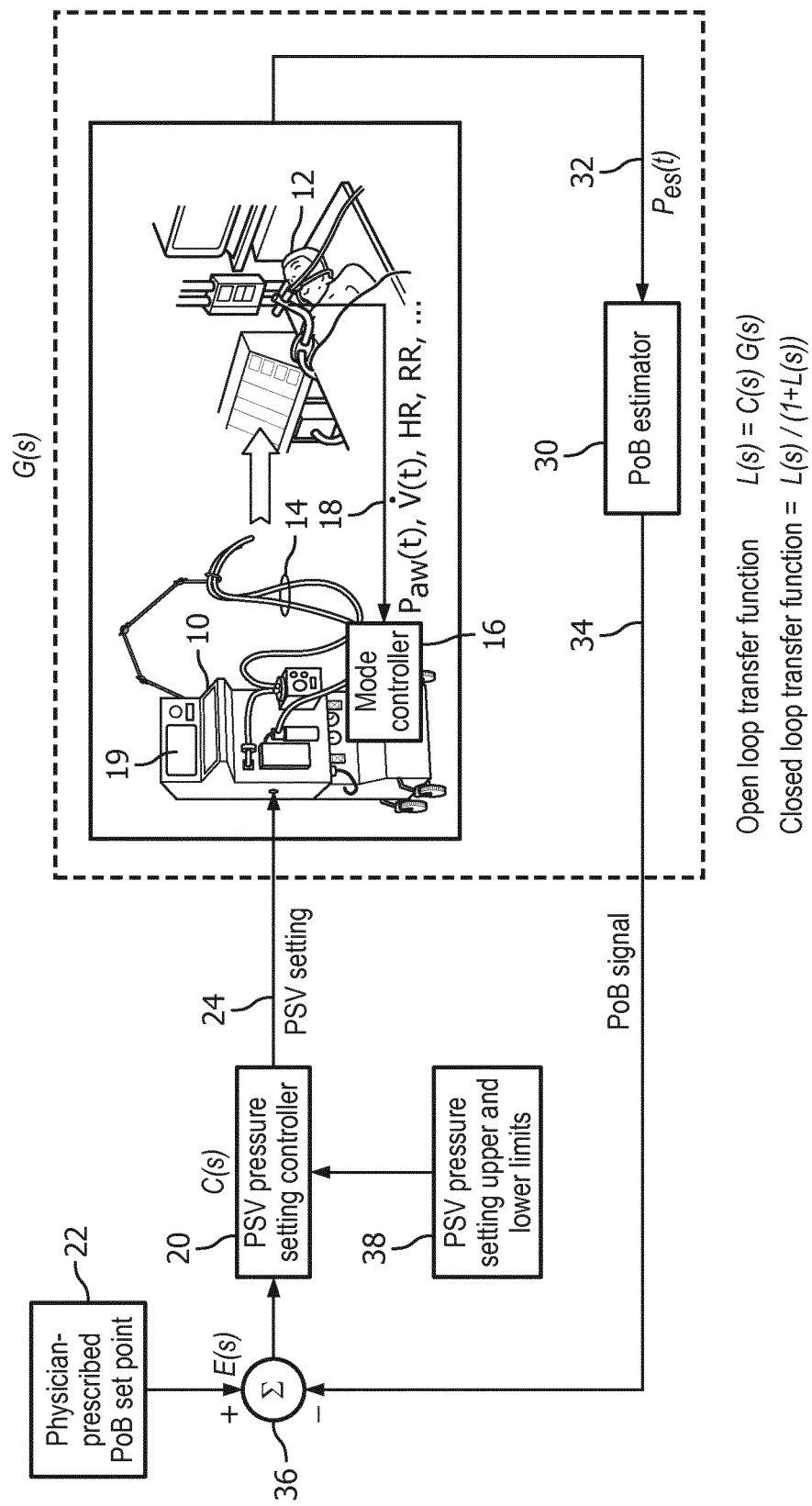
FIG. 1 diagrammatically illustrates a mechanical ventilator system providing Pressure Support Ventilation (PSV) and further including an outer control loop which controls the PSV pressure setting to achieve patient spontaneous respiration with a physician-prescribed Power of Breathing (PoB) level.
Figure 2:
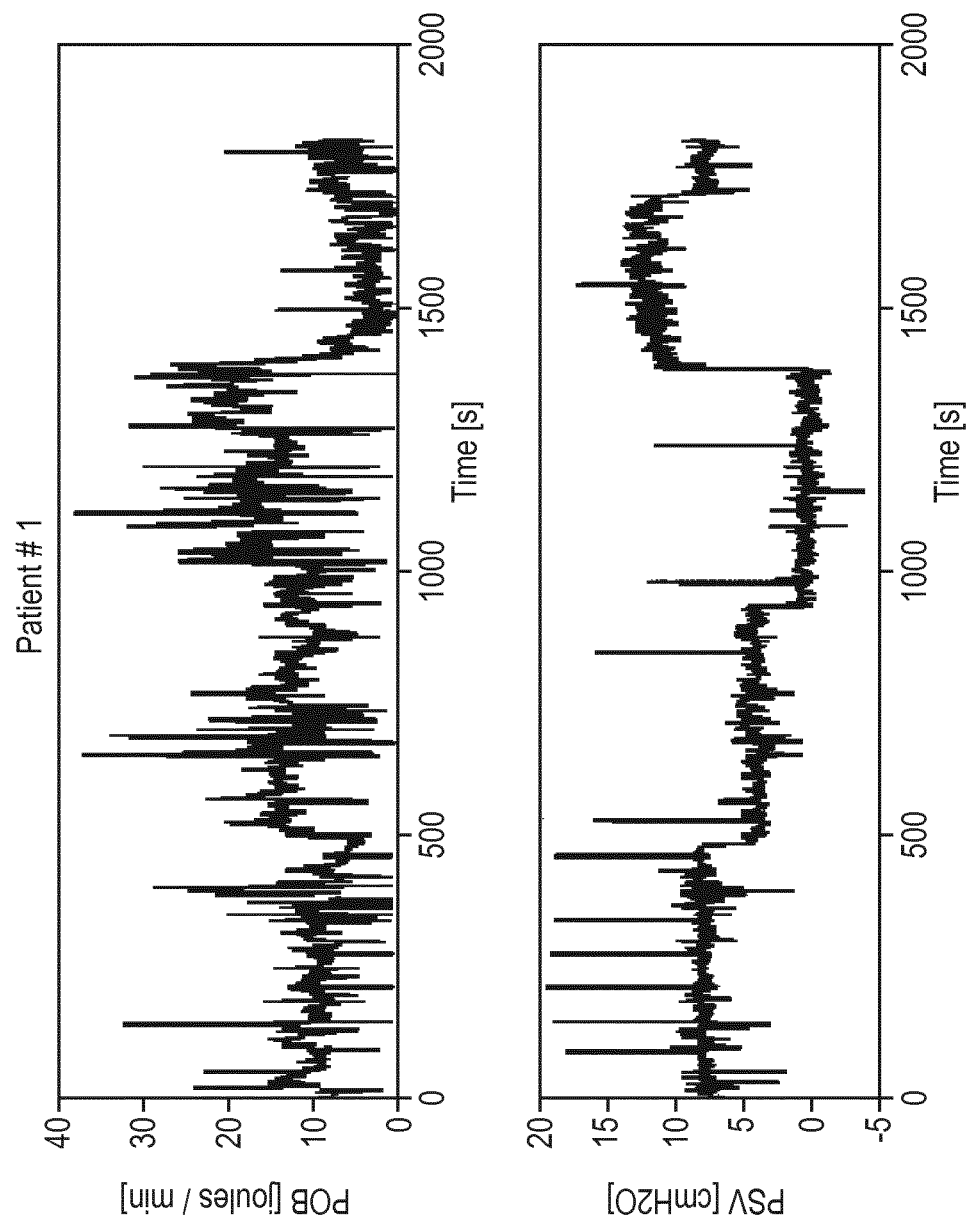
FIGS. 2-6 show experimental PoB data (top plot) and PSV pressure setting (bottom plot) for ventilator/patient systems including a Patient #1 (FIG. 2), a Patient #2 (FIG. 3), a Patient #3 (FIG. 4), a Patient #4 (FIG. 5), and a Patient #5 (FIG. 6).
Figure 3:
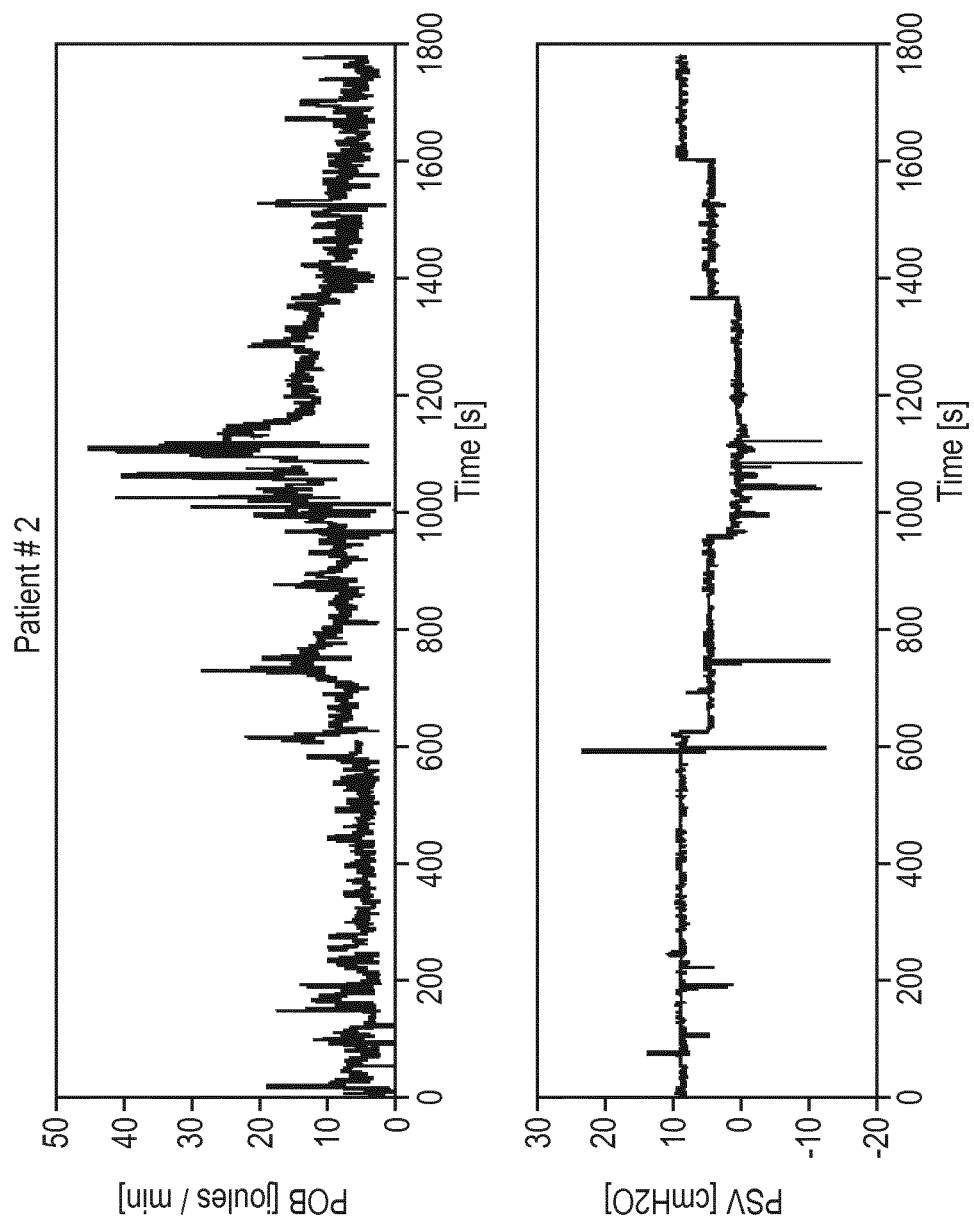
Figure 4:
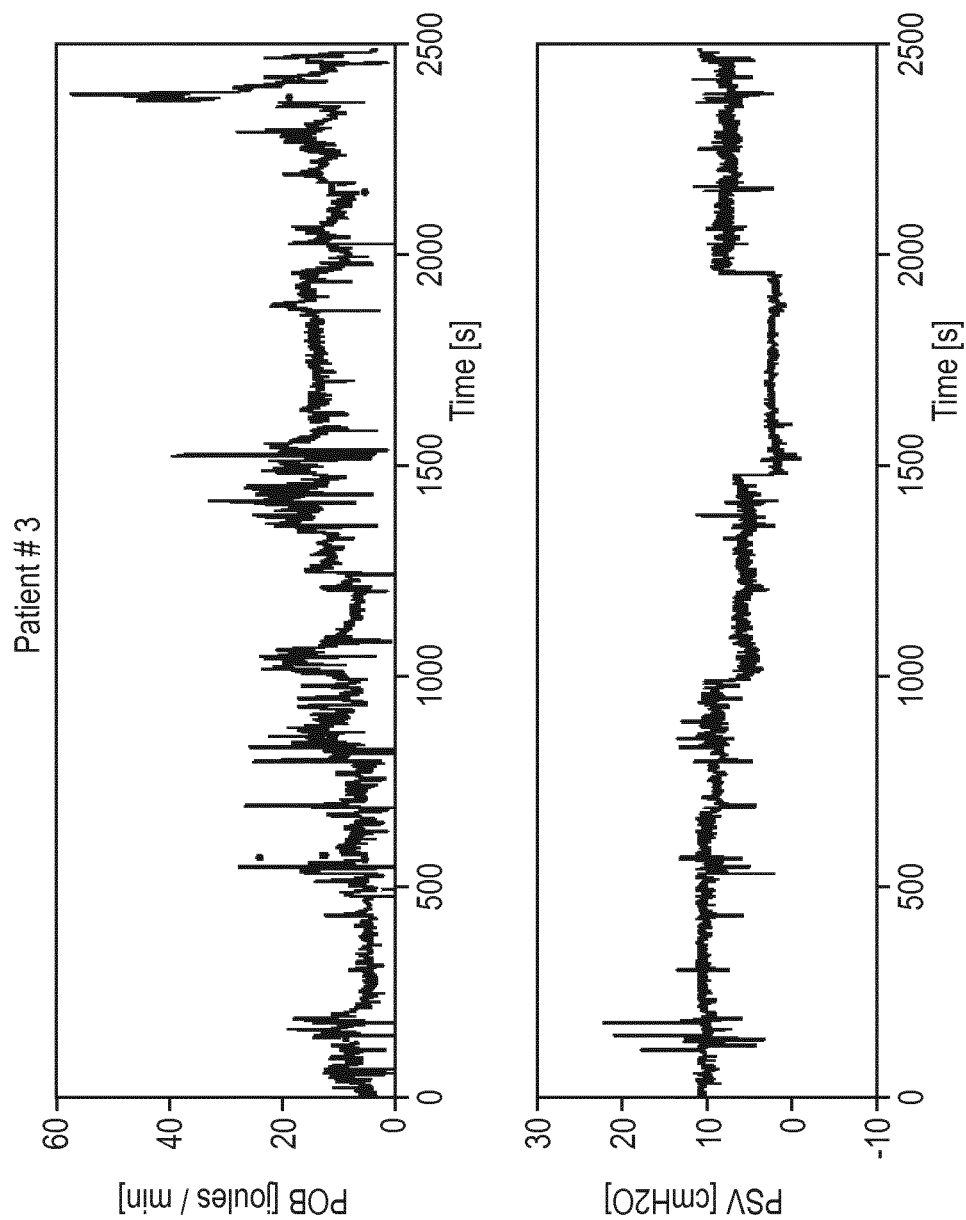
Figure 5:
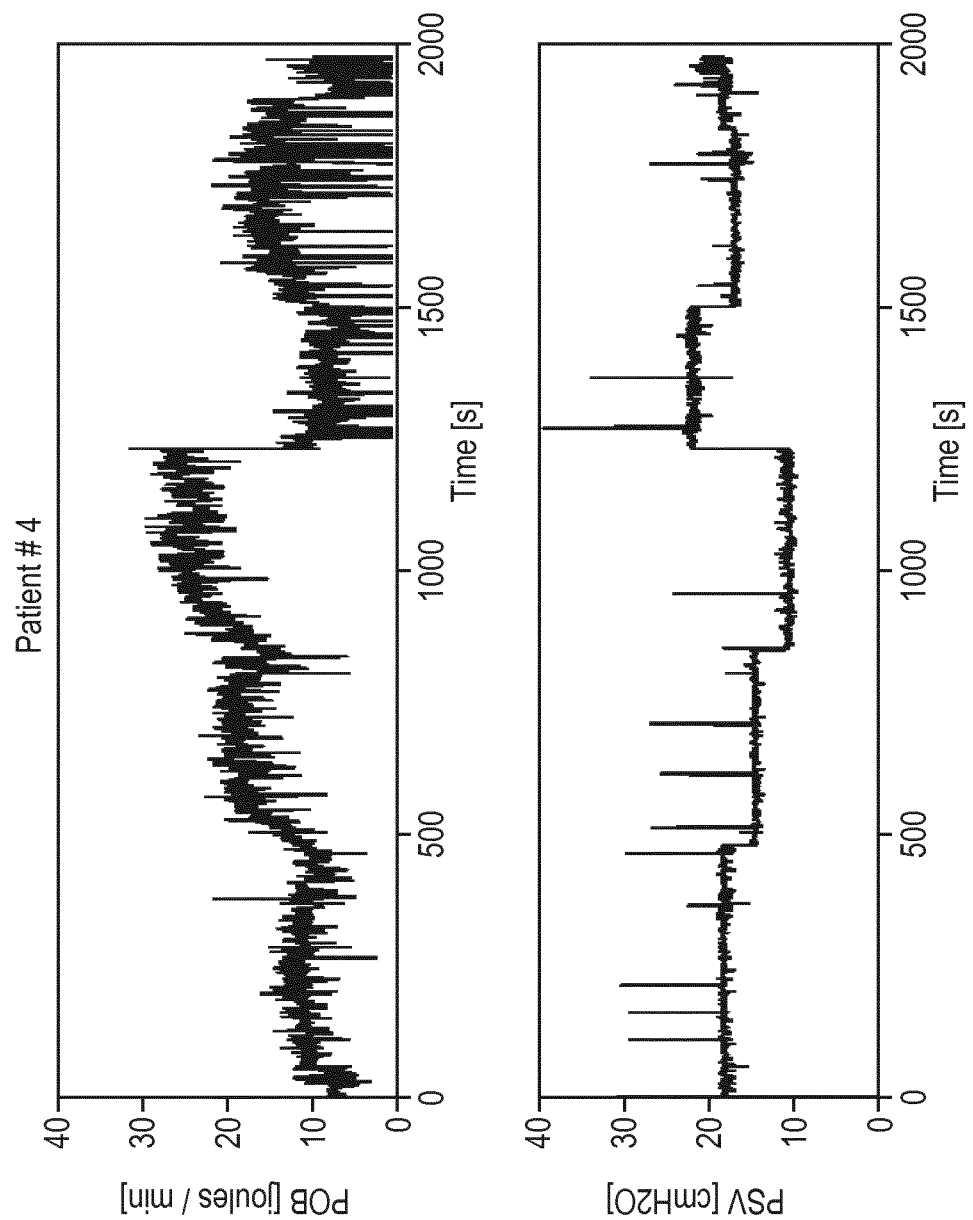
Figure 6:
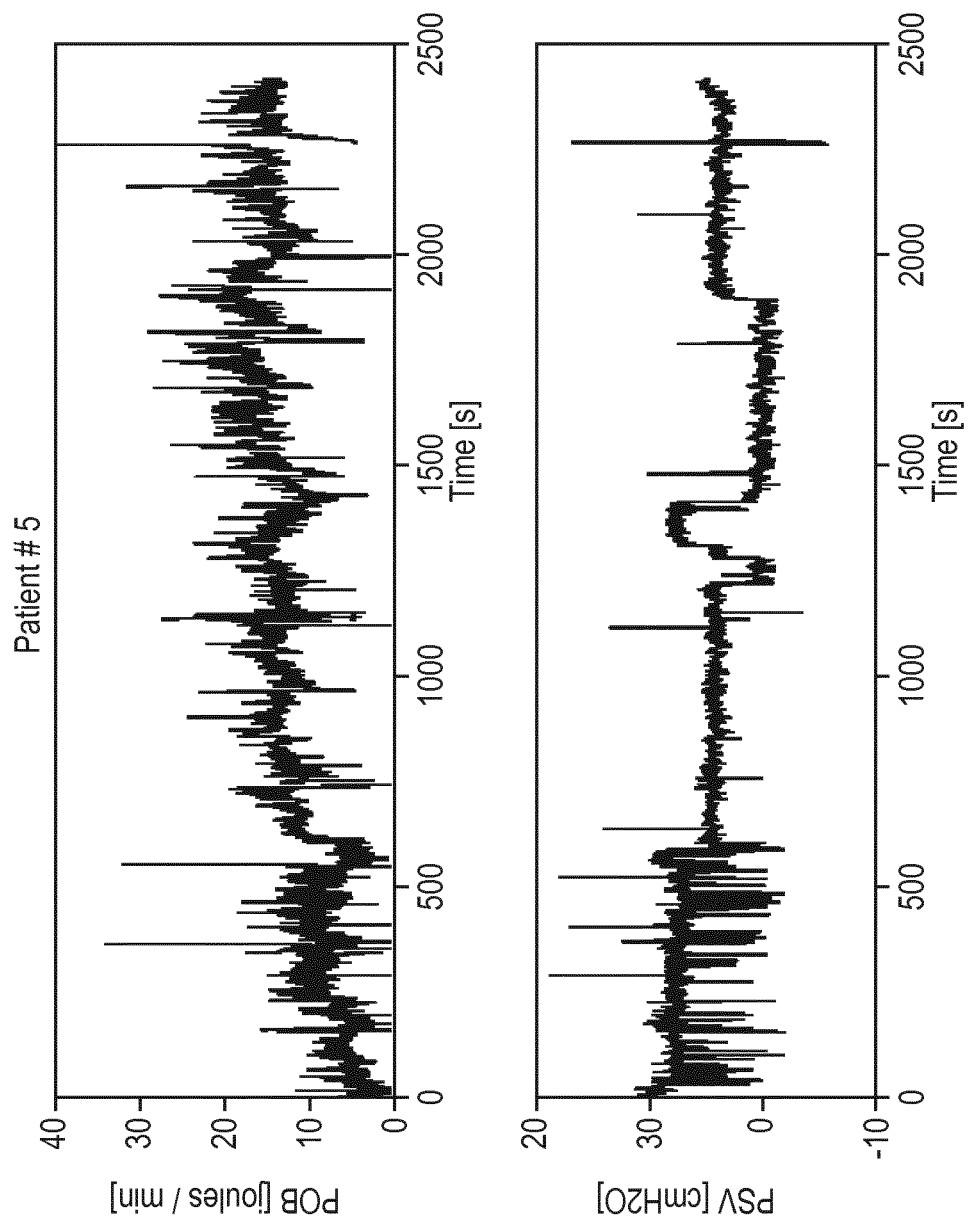

In illustrative examples herein, a mechanically ventilated spontaneously breathing patient is ventilated using pressure support ventilation (PSV), with or without intermittent mandatory ventilation (IMV). In the applied PSV or PSV/IMV ventilation mode, the mechanical ventilator detects the onset of a spontaneous breath and provides pressure support for the breath in accord with a PSV pressure setting. The pressure support waveform may take various forms, e.g. a square wave of amplitude equal to the PSV pressure setting, or an increasing pressure ramp in which the ramp peak equals the PSV pressure setting (or the ramp average or other ramp amplitude characteristic equals the PSV pressure setting), or a decreasing pressure ramp, parabolic pressure waveform, or so forth. The ventilator settings of the applied PSV or PSV/IMV ventilation mode may also include one or more trigger parameters, such as (by way of illustration) a negative pressure threshold wherein airway pressure falling below this threshold is detected as onset of a spontaneous breath, and/or an air flow threshold wherein airway air flow rate above this threshold is detected as onset of a spontaneous breath. If the patient is being oxygenated, the fraction of inspired oxygen ($FiO_2$) is another ventilator setting. If a PSV/IMV mode is being applied, then one or more IMV mandatory breath cycle settings are also provided. Still further ventilator settings may be provided, such as a maximum inflation volume or other safety-related limits.

It is recognized herein that, of these PSV or PSV/IMV parameters, the PSV pressure setting is the primary parameter for effectively tailoring the PSV or PSV/IMV ventilation to elicit the desired work of breathing (WoB) or power of breathing (PoB) from the patient. Accordingly, in embodiments disclosed herein the PSV pressure setting is the only automatically controlled ventilator setting.

It is further recognized herein that the PSV pressure setting can be controlled based on measured WoB or PoB using a classical feedback control system in which the combination of the ventilator and the patient, along with the PoB or WoB estimator, is treated as the controlled system having a transfer function G(s) which is controlled by a controller having a transfer function C(s). A transfer function is the ratio of the output to the input of a system (or sub-system), and a transfer function is represented herein in the (complex) frequency domain by its Laplace transform, i.e. for a time-domain transfer function $$f(t) = \frac{\text{output}(t)}{\text{input}(t)}$$

where t denotes time, the corresponding s-domain representation of this transfer function is formally computed as its Laplace transform $F(s) = \int_0^\infty e^{-st} f(t) dt$ where s is the complex frequency. In quantitative examples herein the time domain is measured in seconds (sec) and the s-domain is in units of $\text{sec}^{-1}$, although of course other time/frequency units can be employed. Using this classical control paradigm for controlling a mechanical ventilator providing mechanical ventilation to a patient in a PSV or PSV/IMV mode in accordance with a PSV pressure setting, the output of the controlled ventilator/patient system is a WoB or PoB signal, and the control input to the controlled ventilator/patient system is the PSV pressure setting. The WoB or PoB signal is represented herein as PoB(s) in the s-domain, that is, in illustrative examples presented herein the power of breathing (PoB) is employed. The PoB is power per unit time (e.g. having units of Joules/sec), whereas WoB is power per breath (e.g. having units of Joules/breath). Either PoB or WoB can be used as the output signal of the controlled ventilator/patient system, but PoB has an advantage in that it does not depend on the generally non-uniform breath interval of a spontaneously breathing patient. In a suitable approach, if WoB is measured it may be converted to PoB using the breath time interval.

The transfer function of the controlled ventilator/patient system is represented as transfer function $$G(s) = \frac{PoB(s)}{PSV(s)}.$$

It is recognized that a difficulty with the disclosed classical control approach is that G(s) is, in part, a function of the patient. This means that the characteristics of the controlled system will change each time the mechanical ventilator is connected with a different patient, and any time the current patient's respiratory characteristics change in a material way. Depending upon the patient, or the patient's current condition, it is therefore possible that the closed loop transfer function $$\frac{C(s)G(s)}{1 + C(s)G(s)}$$

could become unstable. Control instability in the control of life-sustaining mechanical ventilation is generally unacceptable. This difficulty is addressed herein by two approaches, which may optionally be combined. First, it is shown herein that by appropriate empirical design of the controller transfer function C(s) using measured ventilated patient data comprising the measured PoB(s) and control signal PSV(s), the controller transfer function C(s) can be designed so that the closed loop transfer function is stable for a wide range of patients.

Second, in some embodiments disclosed herein the controller is adaptive. In these embodiments, the controlled ventilator/patient system transfer function $$G(s) = \frac{PoB(s)}{PSV(s)}$$

is modeled using PoB(s) and PSV(s) data are collected for the current patient over a representative time interval. The controller transfer function C(s) is then adjusted, if needed, in order to ensure the closed loop system transfer function $$\frac{C(s)G(s)}{1+C(s)G(s)}$$

is stable for the current patient. This adaptation can be updated periodically to ensure the controller remains a stable.

With reference to FIG. 1, a respiratory therapy device includes a mechanical ventilator 10 that provides mechanical ventilation to a patient 12 via air hoses 14. The mechanical ventilator 10 can be of any design capable of delivering mechanical ventilation in a Pressure Support Ventilation (PSV) or pressure support ventilation/intermittent mandatory ventilation (PSV/IMV) mode. The mechanical ventilator 10 may include various ancillary components such as an air filter, a medical oxygen supply to deliver a prescribed fraction of inspired oxygen ($FiO_2$), a humidifier, or so forth. It will be appreciated that the mechanical ventilator includes a controller, diagrammatically shown and labeled as a "mode" controller 16, which is a microprocessor or microcontroller and ancillary sensors and electronics programmed to operate the mechanical ventilator 10 in a PSV or PSV/IMV mode based on sensor data 18 such as an airway pressure $P_{aw}(t)$ measured by an airway pressure gauge, and airway air flow $\dot{V}(t)$ measured by an airway air flow sensor. Another common control parameter is the respired air volume V(t) which can be computed from the air flow as $V(t)=\int\dot{V}(t)dt$ (where the integral is computed over a single breath, or over a time from start of inspiration of a current breath to the present time, or over some other time interval of interest). The sensor data 18 may include various other physiological parameters may also be monitored by suitable sensors such as heart rate (HR), respiratory rate (RR), end-tidal carbon dioxide ($etCO_2$, measured by capnography), or so forth. These data may be displayed on a display component 19 of the mechanical ventilator 10, and/or on a bedside patient monitor or so forth. To provide pressure support in the PSV or PSV/IMV mode, the mode controller 16 detects the onset of spontaneous inspiration (i.e. start of a breath intake), for example as an abrupt decrease in airway pressure $P_{aw}(t)$ and/or an abrupt increase in air flow $\dot{V}(t)$. Thresholds for this detection may be physician-prescribed parameters or default values of the mechanical ventilator 10. Upon detection of onset of a spontaneous breath intake, the mechanical ventilator 10 applies pressure at a PSV pressure setting to support the patient's spontaneous inhalation effort. This pressure may be provided in accord with a prescribed or default pressure support-over-time profile, e.g. a square wave (pressure support at a constant magnitude over the breath) or with some ramp or other profile feature(s). The pressure support may be terminated after a fixed time interval, or may be terminated based on detection of the end of the patient's spontaneous breath intake effort.

If the mode controller 16 is implementing a PSV/IMV mode, then in addition to providing the foregoing pressure support for spontaneous breaths, the mode controller 16 additionally triggers ventilator-driven (i.e. mandatory) breaths if the spontaneous breaths alone do not provide a prescribed or default minimum level of ventilation for the patient (which may be measured based on total number of breaths, and/or inspired air volume, or so forth). In some embodiments, the mode controller 16 implements a PSV/IMV mode in which the intermittent mandatory ventilation is provided in accordance with a synchronized intermittent mandatory ventilation (SIMV) approach in which the timing of any mandatory breaths is synchronized with the spontaneous breaths.

It is to be appreciated that the PSV or PSV/IMV mode may be implemented in the respiratory therapy device of FIG. 1 without modification from conventional PSV or PSV/IMV mode mechanical ventilation. Thus, the physician may prescribe various trigger thresholds or other PSV or PSV/IMV mode parameters as is conventional in the respiratory therapy arts, and the mechanical ventilator 10 implements the PSV or PSV/IMV mode in a conventional manner.

The respiratory therapy device of FIG. 1 differs from a conventional mechanical ventilation device in that it provides an "outer" control loop, that is, a control loop that is "outside" of the control loop of the mode controller 16. This outer control loop is referred to hereinafter as a single-input, single-output (SISO) closed loop feedback control system or using similar phraseology. The SISO control loop employs classical feedback control using a controller 20 having a transfer function designated herein without loss of generality as C(s). The SISO control loop receives as input a physician-prescribed power of breathing (PoB) set point 22, which is the desired respiratory effort for the patient 12. The controller 20 outputs a control signal 24 in the form of a PSV setting 24 that is input to the mechanical ventilator 10. The ventilator/patient system 26 comprising the mechanical ventilator 10 and the patient 12 operates in accord with the PSV or PSV/IMV settings prescribed by the physician but with the PSV setting equal to the control signal 24. A PoB estimator 30 estimates the PoB exerted by the patient 12 based on sensor data 32. The PoB estimator 30 outputs a measured PoB signal 34 which is compared with the set point PoB 22 by an error calculator 36 configured to compute an error signal E(s) as a difference between the PoB signal 34 and the set point PoB value 22. This error signal E(s) is input to the PSV pressure setting controller 20 which computes the PSV setting 24 as C(s)E(s), that is, the product of the controller transfer function C(s) of the controller 20 and the error signal E(s).

To ensure patient safety, the physician may optionally prescribe lower and upper limits 38 on the PSV setting 24, so that if the product C(s)E(s) goes below the lower limit the control signal is set to the lower limit, and similarly if the product C(s)E(s) goes above the upper limit the control signal is set to the upper limit. Reaching these (or optionally other) physician-prescribed upper or lower limits optionally also sets off an alarm, e.g. a warning displayed on the display component 19 of the mechanical ventilator 10 that the pressure support provided by the mechanical ventilator 10 has reached (or is approaching) an upper or lower limit. More generally, the lower and upper PSV limits 38 may be physician-prescribed values, or may be default limits of the respiratory therapy device. In another embodiment, both are contemplated, e.g. default upper and lower limits and additionally the physician can choose to prescribe a narrower limit (e.g. a lower upper limit than the default, or a higher lower limit than the default).

In a suitable embodiment, the PoB estimator 30 computes the PoB by integrating the respiratory muscle pressure $P_{mus}(t)$, which is the pressure applied by the patient's muscles (primarily the thoracic diaphragm though other thoracic muscles may contribute) over time, i.e. $PoB=\int P_{mus}(t)dt$. In the illustrative embodiment, the respiratory muscle pressure $P_{mus}(t)$ is measured using an esophageal pressure measurement employing a balloon that is inserted inside the esophagus of the patient 12 and outputs sensor data 32 comprising measured esophageal pressure $P_{es}(t)$. The esophageal pressure is assumed to be a good proxy for the pleural pressure and is used, in conjunction with an estimate of respiratory system chest wall compliance $C_{rs}$, to compute the WoB via the so-called Campbell diagram or, equivalently, via explicit computation of $P_{mus}(t)$ and then of PoB. In another contemplated embodiment, respiratory muscle pressure $P_{mus}(t)$ is estimated using an Equation of Motion of the Lungs, e.g. using a first-order Equation of the Lungs given by:

$$P_{aw}(t) = R_{rs}\dot{V}(t) + \left(\frac{1}{C_{rs}}\right)V(t) + P_{mus}(t) + P_0 \qquad (1)$$

where $P_{aw}(t)$ is the measured airway pressure, $\dot{V}(t)$ is the measured air flow, $V(t)$ is the respired air volume, i.e. $V(t)=\int \dot{V}(t)dt$, $R_{rs}$ is the respiratory system resistance, $C_{rs}$ is the respiratory system compliance (or, equivalently, elastance $E_{rs}=1/C_{rs}$ can be substituted in Equation (1)), and $P_0$ is a constant term to account for the pressure at the end of expiration. Thus, in the illustrative embodiment, the sensor inputs 32 to the PoB estimator 30 include airway pressure $P_{aw}(t)$ and flow $\dot{V}(t)$. In one approach, the flow-interrupter technique, also called End Inspiratory Pause (EIP), is used to determine the respiratory system parameters $R_{rs}$ and $C_{rs}$ (or $E_{rs}$) after which $P_{mus}(t)$ is obtained directly from Equation (1). A disadvantage of this approach is that it is invasive insofar as it involves occasional interruption of flow through the airway to perform the EIP respiratory system assessment. Alternatively, Equation (1) may be solved to simultaneously determine $P_{mus}(t)$, $R_{rs}$, and $C_{rs}$ (or $E_{rs}$). In this case Equation (1) is underdetermined since for N samples there are N+2 unknowns (the values of $P_{mus}(t)$ for each of the N samples plus $R_{rs}$ and $C_{rs}$). A piecewise approximation of $P_{mus}(t)$ or other approach for reducing the number of unknowns is contemplated to make the simultaneous solution tractable.

As indicated in FIG. 1, the controlled system has a transfer function $$G(s) = \frac{PoB(s)}{PSV(s)}$$

where PSV(s) is the control input 24 (i.e. the PSV setting) and PoB(s) is the POB signal 34 output by the PoB estimator 30. In accord with classical control theory, the open loop transfer function L(s) of the SISO closed loop control system is L(s)=C(s)G(s). The closed loop transfer function is $$\frac{L(s)}{(1+L(s))} = \frac{C(s)G(s)}{(1+C(s)G(s))}.$$

This closed loop system becomes unstable if $C(s)G(s) \to -1$ and is stable otherwise.

The transfer function $$G(s) = \frac{PoB(s)}{PSV(s)}$$

is, in general, different from patient to patient, and also depends on the patient's current respiratory system condition and general health, state of consciousness, or so forth. Furthermore, the transfer function G(s) may depend on the physician-prescribed or default settings of the PSV or PSV/IMV mode currently in force, such as the trigger settings for triggering pressure support. (As an example, if the operational trigger setting results in some delay in the initiation of pressure support this can lead to increased patient effort and hence higher PoB). This means that G(s) can vary significantly, and the transfer function C(s) of the controller 20 is preferably designed to provide large operational margins for G(s) that encompass a wide range (and preferably all) of the credible variants of the system transfer function G(s). To this end, a representative database is generated for "training" patients under mechanical ventilation. For each training patient, input PSV and output PoB data are collected for different PSV settings. These training data are used for optimizing the controller C(s). In the following, an illustrative design approach for designing the controller 20, and more particularly its transfer function C(s), is described.

With reference to Table 1, in this controller design example training data for five patients designated P1, P2, P3, P4, and P5, respectively, were used for the system modeling. Table 1 lists the age, gender, height, weight, and disease/medical issue of each of these five training patients.

TABLE 1 training patients

| Patient # | Age | Gender | Height | Weight | Disease, Issue |
|---|---|---|---|---|---|
| P1 | 79 | Male | 68 inches | 70 kg | Ischemic gut |
| P2 | 70 | Female | 60 inches | 60 kg | Sepsis, COPD |
| P3 | 55 | Male | 67 inches | 71 kg | Hemopneumothorax |
| P4 | 54 | Male | 67 inches | 76 kg | Sepsis (candidemia) |
| P5 | 77 | Male | 70 inches | 71 kg | Bilateral Pneumonia |

With reference to FIGS. 2-6, each training patient was mechanically ventilated under PSV mode and during the ventilation, the level of pressure support was changed a few times. Also, during the ventilation time, the esophageal pressure is measured using an esophageal balloon. The respiratory muscle pressure $P_{mus}(t)$ was calculated using an estimated value of chest wall compliance, and the PoB was calculated from $P_{mus}(t)$. These acquired training data are plotted in FIGS. 2-6 for patients P1-P5, respectively. Referring back to FIG. 1, the data of FIGS. 2-6 can be understood to have been acquired running the system of FIG. 1 open loop, that is, without using the controller 20. In each of FIGS. 2-6, the top plot shows the measured PoB signal 34 (in units of Joules/min) and the bottom plot shows the input PSV setting 24 (in units of $cmH_2O$), again operating in open loop without use of the controller 20. As seen in FIGS. 2-6, the level of noise or disturbance in the ventilator/patient/PoB estimator system is high, and this noise information was taken into account in the design of the control system.

Figure 7:
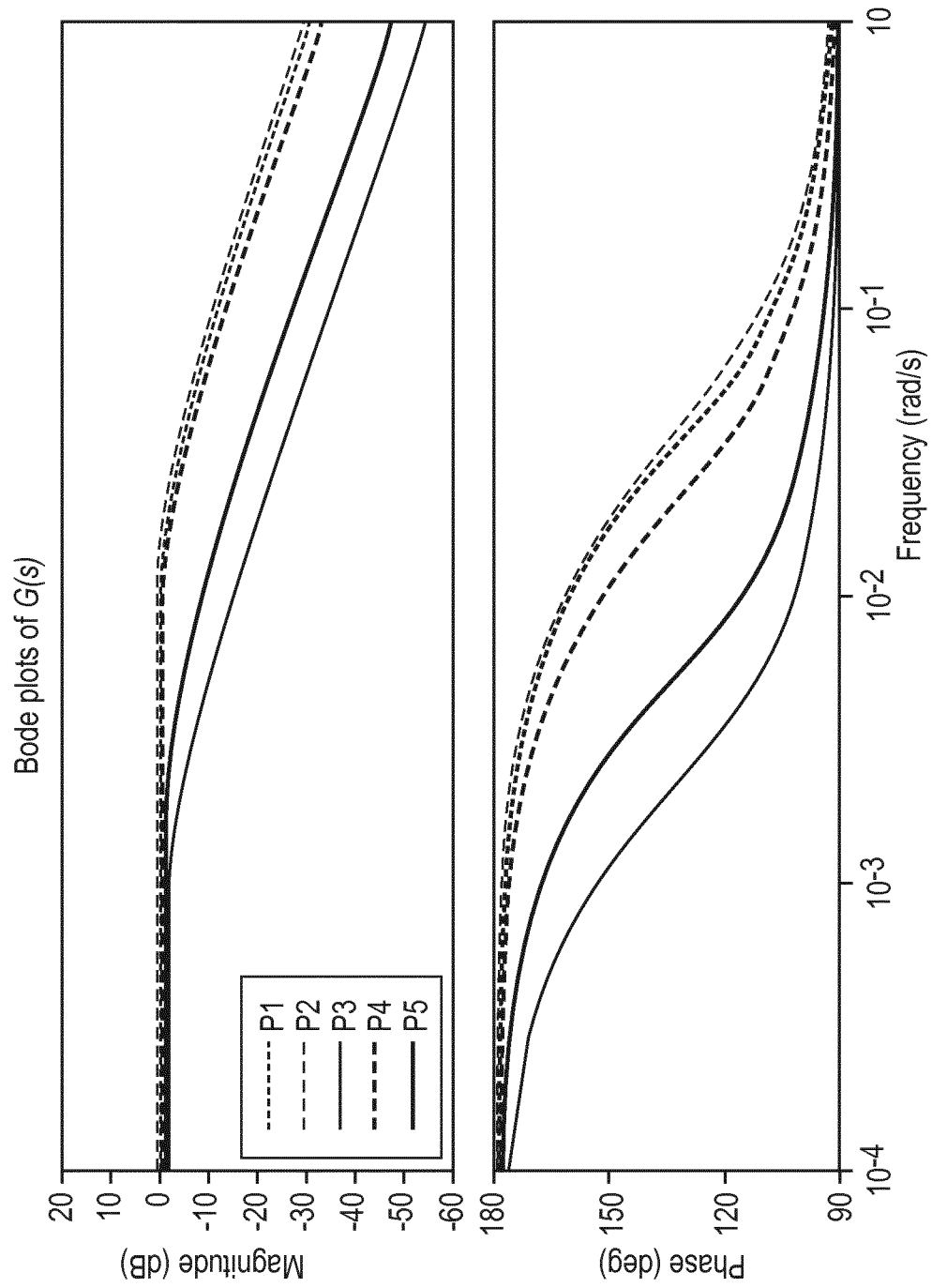
FIG. 7 shows Bode plots (magnitude, upper plot and phase, lower plot) for ventilator/patient system data of Patients #1-#5 presented in respective FIGS. 2-6 fitted to a ventilator-patient system transfer function modeled as $$G(s) = \frac{PoB(s)}{PSV(s)} = K/(\tau s + 1).$$
Figure 8:
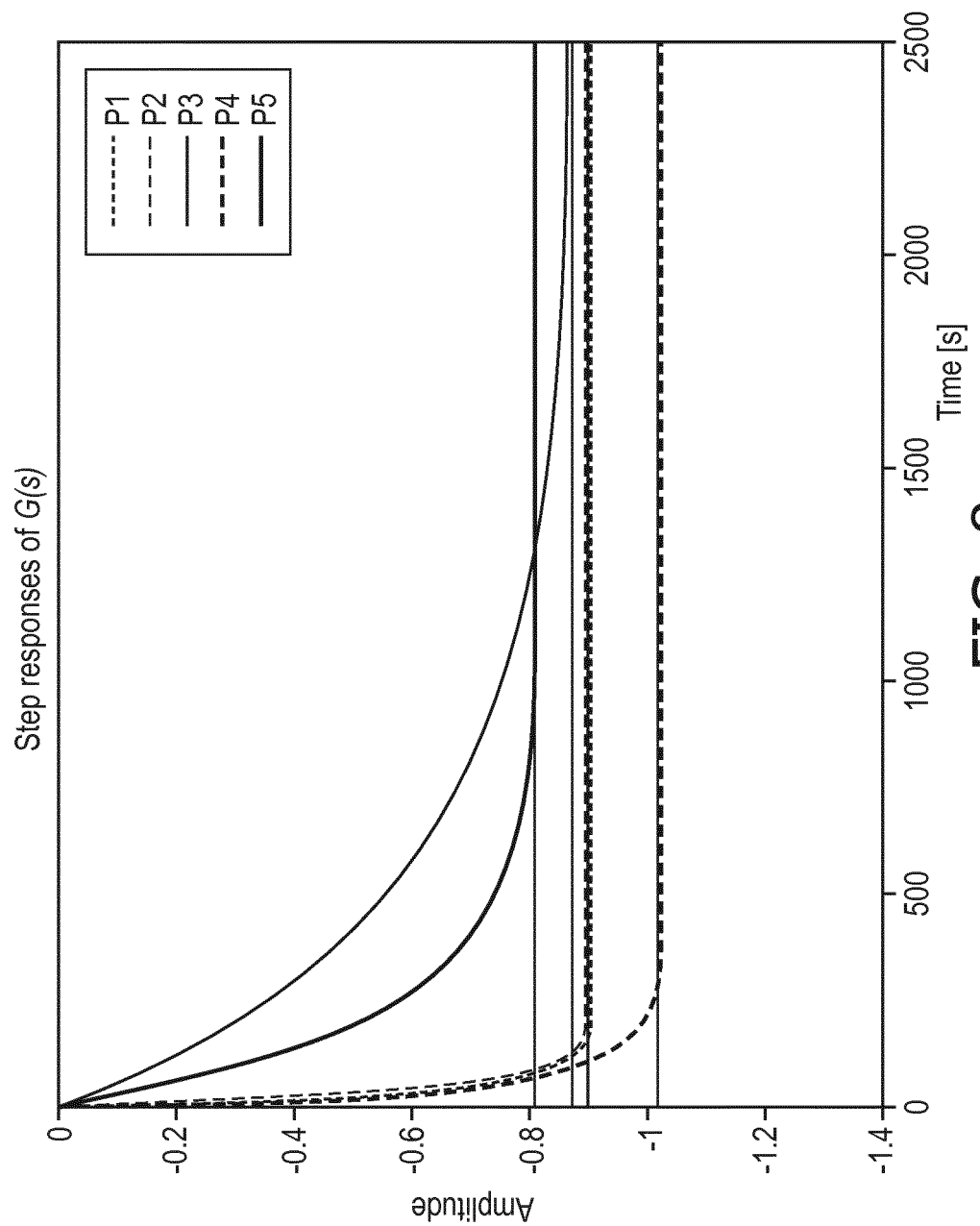
FIG. 8 shows step responses for the ventilator-patient system transfer functions G(s) of FIG. 7.

With reference to FIGS. 7 and 8 and with further reference to Table 2, the training data of FIGS. 2-6 were fitted to a first order dynamic model of the transfer function G(s) of the form:

$$G(s) = \frac{PoB(s)}{PSV(s)} = \frac{K_p}{\tau s + 1} \qquad (2)$$

where PoB(s) is the (open loop) PoB signal 34, PSV(s) is the (open loop) input PSV setting 24, $K_p$ is a gain parameter, and T is a time parameter. Table 2 lists the fitted values for $K_p$ and τ for the ventilator/patient system for each of the five patients P1-P5. FIG. 7 shows the Bode plots of the five open loop ventilator/patient systems. FIG. 8 shows the time-domain step responses of the five open loop ventilator/patient systems. It is noteworthy that although these five ventilator/patient systems are very different in terms of time responses (FIG. 8), the DC gain $K_p$ of all five ventilator/patient systems are within a relatively small range between −0.80 and −1.05. This simplifies the gain selection for the controller transfer function C(s).

TABLE 2

System models for training ventilator/patient systems

| Patient # | $K_p$ (DC gain) | τ (Time constant) |
|---|---|---|
| P1 | −0.90 | 33.3 |
| P2 | −0.90 | 27.7 |
| P3 | −0.87 | 491 |
| P4 | −1.02 | 50.6 |
| P5 | −0.81 | 203.5 |

Figure 9:
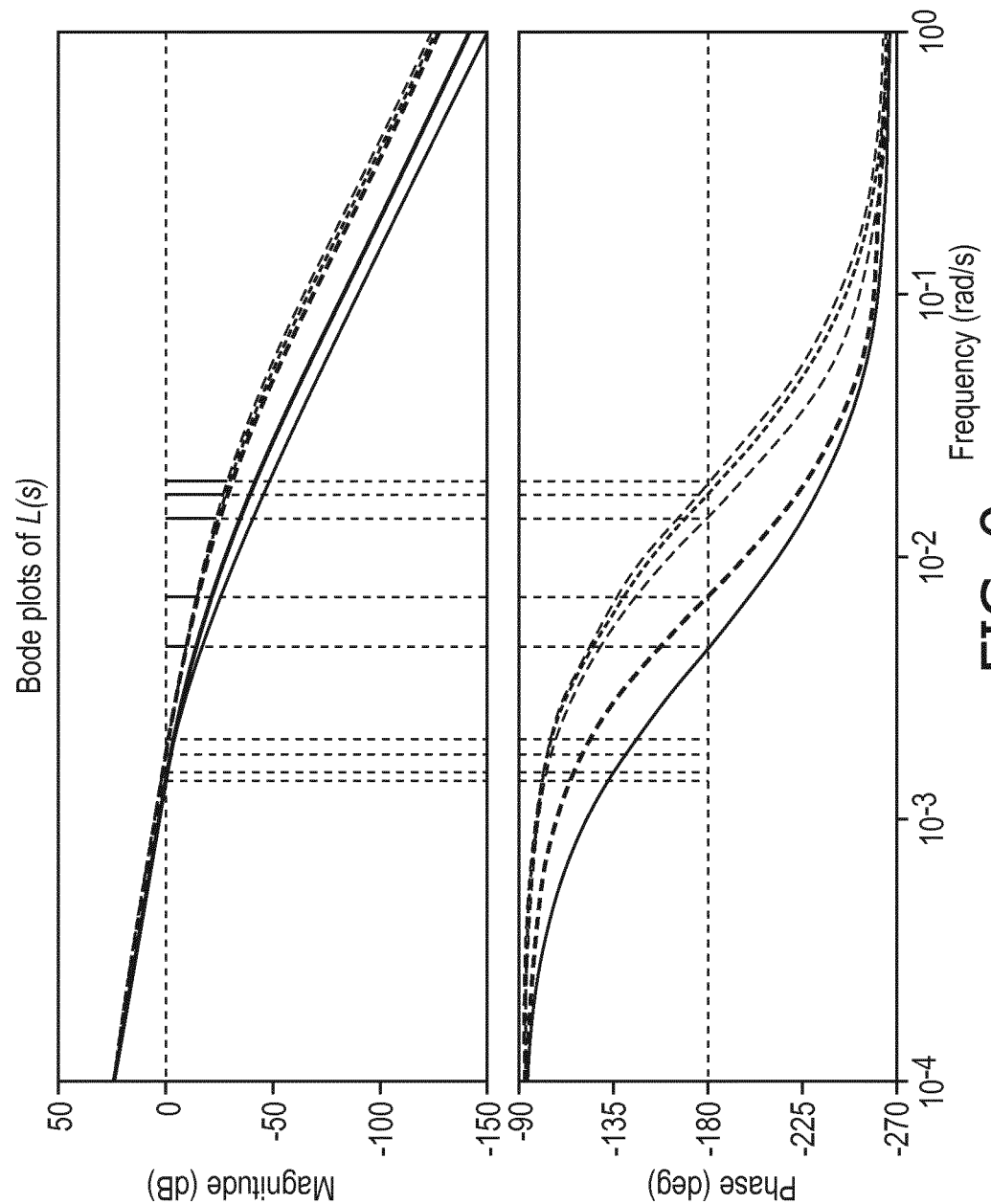
FIG. 9 shows Bode plots of the closed-loop SISO system transfer functions L(s) for a controller designed as described in the text operating with the ventilator/patient systems of FIGS. 7 and 8

With reference now to FIG. 9, design of the controller transfer function C(s) based on the five ventilator/patient training systems is described. From the training data of FIGS. 2-6, it is seen that the noise in the system is at a relatively low frequency. This motivates providing a non-zero, positive-valued pole at relatively low frequency, e.g. a non-zero, positive pole P≤200 sec$^{-1}$ in some contemplated embodiments. Furthermore, the controller 20 should provide zero steady state error this motivates placing another pole at the origin of the s-plane. A suitable controller model is thus:

$$C(s) = \frac{K}{s(s+P)} \quad (3)$$

where P is the noise-suppressing non-zero, positive pole. Designing the values of the controller gain K and noise-suppressing pole P for control of the training systems of Table 2 and FIGS. 7-9 yielded K=0.002 and P=100 sec$^{-1}$ so that the designed controller transfer function was:

$$C(s) = \frac{-0.002}{s(s+100)} \quad (4)$$

The gain K=0.002 and the location P=100 sec$^{-1}$ of the noise-suppressing pole were selected to maximize gain and phase margin for the five training ventilator/patient systems of Table 2 and FIGS. 2-6. FIG. 9 shows the Bode plots of the closed-loop SISO system transfer functions L(s) for the controller C(s) of Equation (4) operating with the ventilator/patient systems of FIGS. 7 and 8. Table 3 lists the gain margin (GM), phase margin (PM), and bandwidth (BW) achieved for each patient by the designed controller.

TABLE 3 margins of stability

| Patient # | GM (dB) | PM (Deg) | BW (rad/sec) |
|---|---|---|---|
| P1 | 29 | 76 | (.00178) |
| P2 | 28 | 77.1 | (.00177) |
| P3 | 16.8 | 47.1 | (.00142) |
| P4 | 23.3 | 73 | (.00199) |
| P5 | 19.3 | 64 | (.00153) |

Figure 10:
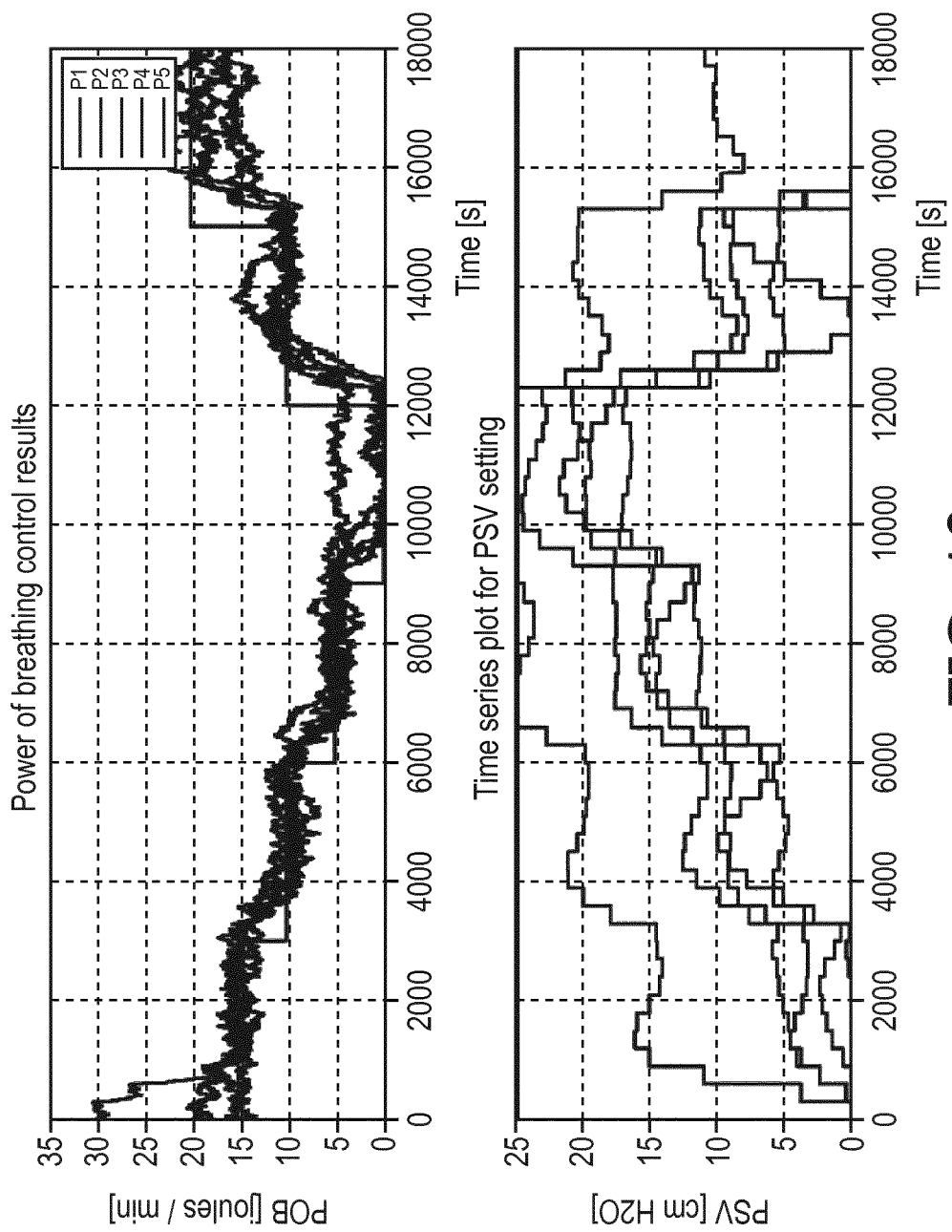
FIG. 10 plots simulated PoB (top plot) for input PSV pressure setting (bottom plot) for the closed-loop transfer function L(s)/(1+L(s)) where L(s) are the five open-loop system transfer functions of FIG. 9.

With reference now to FIG. 10, the controller design of Equation (4) was simulated on the ventilator/patient models of Equation (2) and Table 2. In these simulations, the PSV level was updated every 5 minutes, with the PSV updates discretized to a minimum PSV level change of 1 cmH$_2$O up or down. The maximum allowable PSV change step was 5 cmH$_2$O (that is, the largest change in PSV setting at a single 5 minute interval). The PSV lower and upper limits 38 were 0 cmH$_2$O and 25 cmH$_2$O, respectively. FIG. 10 shows the simulation results, which exhibited stable responses for all five ventilator/patient systems.

With returning reference to FIG. 1, when the respiratory therapy device is started an initial or starting PSV setting is suitably chosen, e.g. prescribed by the physician (preferably) or a default initial PSV setting may be used. The controller 20 then adjusts the PSV setting 24 based on accumulating history of the PoB signal 34 and thereby accumulating error history E(s).

It will be appreciated that the controller represented by the transfer function C(s) of Equation (3) is an illustrative example which has been demonstrated to work well for the representative ventilator/patient systems used in the training. Other controller designs are contemplated. For example, adding a zero to the controller transfer function is contemplated to provide a faster transient response. Another contemplated variant is to add a second, higher frequency positive pole, e.g. at a value greater than 200 sec$^{-1}$, which could beneficially suppress higher frequency noise if present.

The respiratory therapy device of FIG. 1 using a controller transfer function in accord with Equation (3) has been shown to provide large margins for the five training ventilator/patient systems. However, it is further disclosed herein that additional stability can be obtained by constructing the controller 20 to be an adaptive controller. This may be useful, for example, if the controller 20 is to be used with a wider range of patient types (e.g. both infants and elderly patients), or with a number of different types of mechanical ventilators, patient accessories, or so forth.

Figure 11:
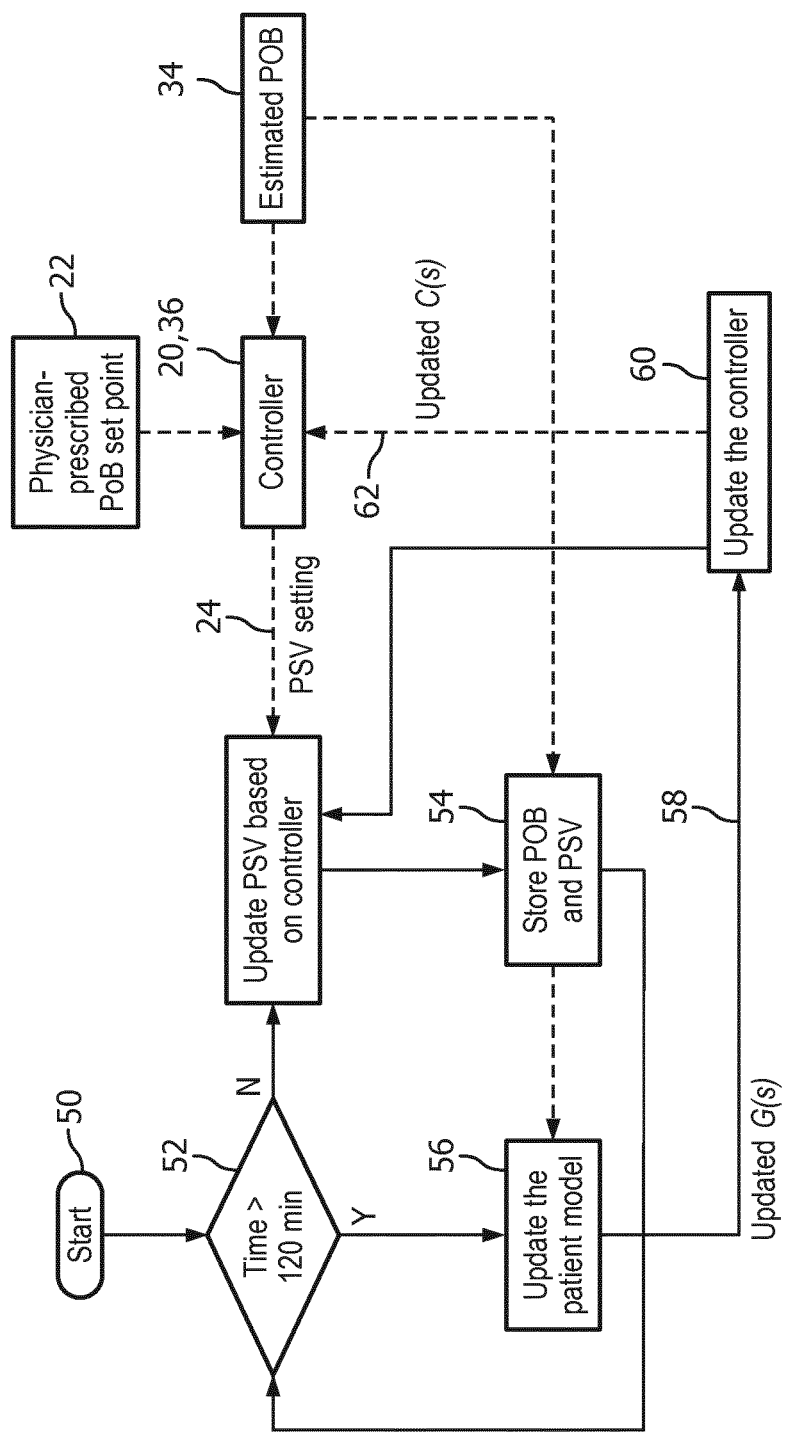
FIG. 11 illustrates a patient adaptation component optionally added to the single input, single output (SISO) closed loop controller of FIG. 1.

With continuing reference to FIG. 1 and with further reference to FIG. 11, an adaptive variant of the controller 20 is described. Diagrammatically indicated in FIG. 11 are the controller 20 (grouped with the error calculator 36 as a unit in FIG. 11), the physician-prescribed PoB set point 22, and the estimated PoB signal 34. Also indicated in FIG. 11 is the PSV setting 24 output by the controller 20. The start of patient ventilation is indicated in FIG. 1 by a "start" block 50. The variant of FIG. 11 adds a patient adaptation component including blocks 52, 54, 56, 60. After ventilator startup 50, the SISO closed-loop feedback controller runs for a pre-set time (two hours, i.e. 120 min, in the illustrative example of FIG. 11) to collect sufficient data to perform controller adaptation. A delay block 52 diagrammatically shows implementation of this initial delay. During this delay, PoB and PSV setting data are collected and stored in operation 54. When the pre-set time interval (e.g. 120 min) has passed, flow passes to a ventilator/patient model update operation 56, which updates G(s). In the illustrative example of using a first-order dynamic model of the transfer function G(s), this can be done by fitting the first-order model of Equation (2) to optimize $K_p$ and τ respective to the collected (PSV(t), PoB(t)) data after transforming PSV(t) and PoB(t), respectively, into the s-domain using the Laplace transform. The resulting updated G(s) 58 is input to a controller update operation 60 which updates the controller transfer function C(s) to provide large-margin control of the ventilator/patient represented by the updated G(s) 58. For the controller transfer function model of Equation (3), this can be done by optimizing the controller gain K and pole P parameters so that the closed-loop transfer function $$\frac{C(s)G(s)}{(1+C(s)G(s))}$$

with the updated G(s) 58 provides large gain and phase operating margins. The resulting updated controller transfer function C(s) 62 is loaded into the controller 20 for subsequent use in controlling the mechanical ventilator 10.

The outer loop components (e.g. controller 20, PoB estimator 30, error calculator 36, and optional controller adaptation components shown in FIG. 11) may be implemented as one or more electronic components separate from the mechanical ventilator 10. For example, in one embodiment the controller 20, PoB estimator 30, and error calculator 36 are constructed as a unitary add-on control box including a microprocessor or microcontroller and ancillary circuitry, and having a port outputting the PSV setting 24 via a cable to the mechanical ventilator 10 and having an input port receiving the esophageal pressure reading 32 from an esophageal catheter.

Alternatively, some or all of the outer loop components can be integrated with the mechanical ventilator 10. In this case the controller 20, PoB estimator 30, and error calculator 36 are suitably implemented on the same microprocessor that is programmed to implement the mode controller 16. In this embodiment the PSV setting 24 is conveyed to the mode controller 16 in software, e.g. as an argument of a call function or so forth, and the mechanical ventilator 10 is modified only in providing an input port to receive the esophageal pressure reading 32. In a variant embodiment, if the PoB signal 34 is calculated using an Equation of Motion of the Lungs (e.g. the first order Equation of Motion of the Lungs of Equation (1)), and as the mechanical ventilator 10 typically already receives the airway pressure $P_{aw}(t)$ and air flow $\dot{V}(t)$ as inputs, the outer loop can be implemented on the same microprocessor of the mechanical ventilator 10 which implements the mode controller 16 without adding any additional input or output ports or other hardware.

It will be further appreciated that various functionality of the outer loop (and optionally also the mode controller 16) may be implemented as a non-transitory storage medium storing instructions executable on the microprocessor of the mechanical ventilator 10 and/or on a separate microprocessor to perform the disclosed control functionality (optionally with a adaptation as described with reference to FIG. 11). The non-transitory storage medium may, for example, comprise a flash memory or other solid state electronic storage device or component, a magnetic disk or other magnetic storage device or component, an optical disk or other optical storage device or component, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A respiratory therapy device comprising:
a mechanical ventilator configured to provide mechanical ventilation to a patient in a pressure support ventilation (PSV) or pressure support ventilation/intermittent mandatory ventilation (PSV/IMV) mode in accordance with a PSV pressure setting;
a power of breathing (PoB) or work of breathing (WoB) estimator configured to generate a PoB or WoB signal for the patient;
an error calculator configured to compute an error signal E (s) as a difference between the PoB or WoB signal and a set point PoB or WoB value; and
a controller having a controller transfer function C(s) and configured to input the PSV pressure setting equal to C(s)E(s) to the mechanical ventilator to control operation of the mechanical ventilator in providing mechanical ventilation to the patient,
wherein the mechanical ventilator, the PoB or WoB estimator, the error calculator, and the controller are operatively interconnected to form a single-input, single-output (SISO) closed loop feedback control system in which the mechanical ventilator and the PoB or WoB estimator define the controlled system whose single input is the PSV pressure setting and whose single controlled output is the PoB or WoB signal,
wherein the controlled system has a controlled system transfer function G(s) given by:

$$G(s) = \frac{PoB(s)}{PSV(s)} = \frac{K_p}{\tau s + 1}$$

where PoB(s) is the PoB or WoB signal, $K_p$ is a gain parameter, r is a time parameter, and PSV(s) is the PSV pressure setting, and the respiratory therapy device further comprises:
an electronic device programmed to fit $K_p$ and r to (PoB(s), PSV(s)) data generated by the operating SISO closed loop feedback control system and to adjust parameters of the controller transfer function C(s) to maintain stability of the closed loop transfer function $$\frac{C(s)G(s)}{1+C(s)G(s)}$$

of the SISO closed loop feedback control system.

2. A respiratory therapy device comprising:
a mechanical ventilator configured to provide mechanical ventilation to a patient in a pressure support ventilation (PSV) or pressure support ventilation/intermittent mandatory ventilation (PSV/IMV) mode in accordance with a PSV pressure setting;
a power of breathing (PoB) or work of breathing (WoB) estimator configured to generate a PoB or WoB signal for the patient;
an error calculator configured to compute an error signal E (s) as a difference between the PoB or WoB signal and a set point PoB or WoB value; and
a controller having a controller transfer function C(s) and configured to input the PSV pressure setting equal to C(s)E(s) to the mechanical ventilator to control operation of the mechanical ventilator in providing mechanical ventilation to the patient, wherein the mechanical ventilator, the PoB or WoB estimator, the error calculator, and the controller are operatively interconnected to form a single-input, single-output (SISO) closed loop feedback control system in which the mechanical ventilator and the PoB or WoB estimator define the controlled system whose single input is the PSV pressure setting and whose single controlled output is the PoB or WoB signal, the respiratory therapy device further comprising an electronic device programmed to fit parameters of a model of a controlled system transfer function G(s) given by:

$$G(s) = \frac{PoB(s)}{PSV(s)}$$

where PoB(s) is the PoB or WoB signal and PSV(s) is the PSV pressure setting to (PoB(s), PSV(s)) data generated by the operating SISO closed loop feedback control system and to adjust parameters of the controller transfer function C(s) to maintain stability of the closed loop transfer function $$\frac{C(s)G(s)}{1+C(s)G(s)}$$

of the SISO closed loop feedback control system.

3. A respiratory therapy device comprising:
a mechanical ventilator configured to provide mechanical ventilation to a patient in a pressure support ventilation (PSV) or pressure support ventilation/intermittent mandatory ventilation (PSV/IMV) mode in accordance with a PSV pressure setting;
a power of breathing (PoB) or work of breathing (WoB) estimator configured to generate a PoB or WoB signal for the patient;
an error calculator configured to compute an error signal E(s) as a difference between the PoB or WoB signal and a set point PoB or WoB value; and
a controller having a controller transfer function C(s) and configured to input the PSV pressure setting equal to C(s)E(s) to the mechanical ventilator to control operation of the mechanical ventilator in providing mechanical ventilation to the patient,
wherein the mechanical ventilator, the PoB or WoB estimator, the error calculator, and the controller are operatively interconnected to form a single-input, single-output (SISO) closed loop feedback control system in which the mechanical ventilator and the PoB or WoB estimator define the controlled system whose single input is the PSV pressure setting and whose single controlled output is the PoB or WoB signal;
wherein the controller transfer function C(s) is given by:

$$C(s) = \frac{-K}{s(s+P)}$$

where K is a controller gain having a positive value, P is a noise-suppressing pole having a positive value and where s is a complex frequency.

4. The respiratory therapy device of claim 3 wherein C(s) includes a pole at zero and a pole with a positive value P.

5. The respiratory therapy device of claim 3 wherein $P \leq 200$ sec$^{-1}$.

6. A single input, single output (SISO) closed-loop controller for controlling a mechanical ventilator) configured to provide mechanical ventilation to a patient in a pressure support ventilation (PSV) or pressure support ventilation/intermittent mandatory ventilation (PSV/IMV) mode in accordance with a PSV pressure setting, the closed-loop controller comprising:
a power of breathing (PoB) or work of breathing (WoB) estimator) configured to generate a signal representing PoB or WoB of the patient;
an error calculator configured to compute an error signal E (s) as a difference between the signal representing PoB or WoB of the patient and a set point value; and
a controller having a controller transfer function C(s) and configured to generate the PSV pressure setting as the product C(s)E(s) to control operation of the mechanical ventilator in providing mechanical ventilation to the patient; and
an electronic device programmed to fit parameters of a model of a controlled system transfer function G (s), given by $$G(s) = \frac{PoB(s)}{PSV(s)}$$

of the mechanical ventilator providing ventilation to the patient under control of the SISO closed-loop controller to PoB (s) and PSV (s) data generated by the operating SISO closed loop controller, where PoB (s) are signal data representing the PoB or WoB of the patient and PSV (s) are PSV pressure setting data, and to adjust parameters of the controller transfer function C(s) to maintain stability of the closed loop transfer function $$\frac{C(s)G(s)}{1+C(s)G(s)}.$$

7. The SISO closed-loop controller of claim 6 further comprising:
an electronic device programmed to fit parameters of a model of the controlled system transfer function of the mechanical ventilator providing ventilation to the patient under control of the operating SISO close-loop controller to PoB (s) and PSV (s) data generated by the operating SISO closed loop controller, where PoB (s) are signal data representing the PoB or WoB of the patient and PSV (s) are PSV pressure setting data, and to adjust parameters of the controller transfer function C(s) to maintain stability of the operating SISO closed-loop controller.

8. The SISO closed-loop controller of claim 6 wherein the controller has programmed upper and lower limits for the PSV pressure setting.

9. The SISO closed-loop controller of claim 6 wherein the controller transfer function C(s) is given by:

$$C(s) = \frac{-K}{s(s+P)}$$

where K is a controller gain having a positive value, P is a noise-suppressing pole having a positive value and where s is a complex frequency.

10. The SISO closed-loop controller of claim 9 wherein C(s) includes a pole at zero and a pole with a positive value P.

11. The SISO closed-loop controller of claim 9 wherein $P \leq 200 \text{ sec}^{-1}$.

12. The SISO closed-loop controller of claim 6 wherein the electronic device is programmed to adjust parameters of the controller transfer function C(s) including at least one non-zero and positive pole of the controller transfer function C(s) to maintain stability of the operating closed-loop controller.

* * * * *